(12) United States Patent
Gandham et al.

(10) Patent No.: US 9,296,770 B2
(45) Date of Patent: Mar. 29, 2016

(54) TETRAOXA DIPHOSPHASPIRO COMPOUNDS

(71) Applicant: RELIANCE INDUSTRIES LIMITED, Mumbai (IN)

(72) Inventors: Satya Srinivasa Rao Gandham, Gujarat (IN); Muthukumaru Subramania Pillai, Gujarat (IN)

(73) Assignee: Reliance Industries Limited, Mumbai (IN)

( * ) Notice: Subject to any disclaimer, the term of this patent is extended or adjusted under 35 U.S.C. 154(b) by 0 days.

(21) Appl. No.: 14/689,192

(22) Filed: Apr. 17, 2015

(65) Prior Publication Data

US 2015/0225434 A1 Aug. 13, 2015

Related U.S. Application Data

(63) Continuation of application No. PCT/IN2013/000634, filed on Oct. 18, 2013.

(30) Foreign Application Priority Data

Oct. 18, 2012 (IN) .......................... 3050MUM2012

(51) Int. Cl.
*C07F 9/6574* (2006.01)
*C08K 5/527* (2006.01)

(52) U.S. Cl.
CPC ......... *C07F 9/65744* (2013.01); *C07F 9/65746* (2013.01); *C08K 5/527* (2013.01)

(58) Field of Classification Search
CPC .. C07F 9/65744; C07F 9/65746; C08K 5/527
See application file for complete search history.

(56) References Cited

U.S. PATENT DOCUMENTS

| | | | |
|---|---|---|---|
| 3,632,858 A | 1/1972 | Milionis et al. | |
| 3,809,675 A | 5/1974 | Hansen | |
| 3,904,582 A | 9/1975 | Hansen | |
| 4,100,132 A | 7/1978 | Hill | |
| 4,147,689 A | 4/1979 | Thompson et al. | |
| 4,305,866 A | 12/1981 | York et al. | |
| 4,413,077 A * | 11/1983 | Valdiserri et al. | ............. 524/120 |
| 4,557,844 A | 12/1985 | Horodysky | |
| 4,739,090 A | 4/1988 | Tajima et al. | |
| 4,888,371 A | 12/1989 | Tajima et al. | |
| 4,985,157 A | 1/1991 | Farng et al. | |
| 5,230,816 A | 7/1993 | Pastor et al. | |
| 5,618,871 A | 4/1997 | Nesvadba | |
| 6,444,733 B1 | 9/2002 | Stadler | |
| 7,498,457 B2 | 3/2009 | Schafter | |
| 2005/0209379 A1 | 9/2005 | Botkin et al. | |
| 2008/0293856 A1 | 11/2008 | Kumar et al. | |
| 2010/0305361 A1 | 12/2010 | Cholli et al. | |

FOREIGN PATENT DOCUMENTS

| | | | |
|---|---|---|---|
| EP | 0705874 A1 | 4/1996 | |
| JP | 06093096 | * 4/1994 | ........... C08G 63/692 |

OTHER PUBLICATIONS

International Search Report regarding Application No. PCT/IN2013/000634, mailed Apr. 22, 2014.

* cited by examiner

*Primary Examiner* — John Uselding
(74) *Attorney, Agent, or Firm* — Harness, Dickey & Pierce, P.L.C.

(57) ABSTRACT

The present disclosure provides tetraoxa diphosphaspiro compound represented by Formula 1.

FORMULA I

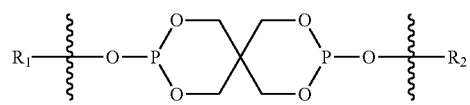

The present disclosure further provides a process for synthesizing the compound represented by Formula 1.

22 Claims, No Drawings

TETRAOXA DIPHOSPHASPIRO COMPOUNDS

CROSS-REFERENCE TO RELATED APPLICATIONS

This application is a continuation of International Application No. PCT/IN2013/000634, filed Oct. 18, 2013. This application claims priority to Indian Application No. 3050/MUM/2012, filed Oct. 18, 2012. The disclosures of the above applications are incorporated herein by reference.

FIELD OF THE DISCLOSURE

The present disclosure relates to diphosphaspiro compounds. More particularly, the present disclosure relates to tetraoxa diphosphaspiro compounds.

BACKGROUND

Many tetraoxa diphosphaspiro compounds of the structure

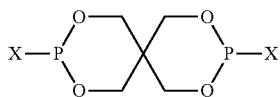

are known in the art. For instance, tetraoxa diphosphaspiro compound where X is 2,4-di-t-butyl-phenyl is disclosed in U.S. Pat. No. 4,305,866. U.S. Pat. No. 4,305,866 also discloses a method for preparing the compound.

U.S. Pat. No. 5,230,816 discloses a compound where X is di(2-ethylhexyl)amino.

Tetraoxa diphosphaspiro have been found to possess activity, for example anti-oxidant activity. An active tetraoxa diphosphaspiro compound may find application in various fields, for example, it may be used as a stabilizing agent for stabilizing various polyolefins.

Polyolefins are a commercially significant class of polymers that can be tailored to achieve a wide range of mechanical and chemical properties; thereby enabling application in a wide variety of products such as agricultural films, garments, tapes, stretch films, retail bags, bottles, containers and pipes.

Polymers as such, are generally processed either by film extrusion or by molding techniques. During the film extrusion process the polymer is heated and in the molten state, is forced through a die to produce films of variable sizes. The molding process comprises heating and compressing the polymer in an extruder, followed by forcing the extrudate into a mould where the said extrudate is left to solidify to any required shape.

Typically, in the aforementioned processes, polymers are subjected to severe processing parameters such as mechanical, thermal, photo and ultra violet stresses. The free radicals generated during these processes initiate a chain reaction and cause polymer degradation. In the most probable event of oxidation/thermal degradation, the processability of the polymers is significantly hampered resulting in poor quality of the final product.

The rate of degradation of the polymer is reduced by incorporating, into the polymeric substrate, a stabilizing agent in the form of an antioxidant. The resultant polymer composition, after addition of antioxidant, becomes comparatively thermo-stable and less susceptible to degradation. The main criteria for an entity to be a good antioxidant is high melting point, medium range molecular weight, miscibility with the polymer and stability during processing at high temperatures.

Antioxidants are generally classified into primary and secondary antioxidants, according to their mode of action. Primary antioxidants mainly act as chain-breaking agents as they rapidly react and neutralize the peroxy radicals (ROO*). Hindered phenols are the traditionally known primary antioxidants and are based on 2,6-di-t-butyl-4-methylphenol (BHT). On the other hand, secondary antioxidants react with hydroperoxides (ROOH) to yield non-radical, non-reactive products and are frequently called hydroperoxide decomposers. Secondary antioxidants are usually organic molecules consisting phosphates.

Use of primary and secondary antioxidants as stabilizing agents has been widely reported. Previously, polyolefins have been melt stabilized by incorporating primary antioxidants, independently or in combination with secondary antioxidants and other additives including various phenolic antioxidants. Other reports include use of thiosemi-carbazide, hindered amine stabilizers and natural antioxidants such as grape seeds and tomato extracts. The use of phenol substituted benzophenones as antioxidants for stabilizing polyolefins has been disclosed in U.S. Pat. No. 3,632,858. U.S. Pat. No. 3,809,675 discloses the retarding action of phenyl hydrazones when incorporated in polypropylene, thus preventing oxidative degradation.

However, a major drawback associated with the use of presently available primary and secondary antioxidants is less efficiency upon independent use. This is because the intrinsic properties of the said antioxidants when used alone are insufficient to bring about maximal polymer stabilization. Therefore, in order to overcome the aforementioned drawback, these two classes of polymers are used in conjunction. The practice nevertheless, is accompanied by notable economic constraints as multiple additives are incorporated into the polymers to achieve the same purpose.

Multifunctional antioxidants are a comparatively newly introduced class of antioxidants. The said class possesses properties of both primary and secondary antioxidants due to their characteristic molecular design. As a result, use of a single multifunctional antioxidant obviates the redundant practice of incorporating multiple antioxidants/additives in the polymer for achieving stabilization.

U.S. Pat. No. 3,904,582 discloses aromatic oxamide, imide or imine derivatives as antioxidants of polyolefins. Certain imido-oxamide type compounds are useful in preventing metal catalysed oxidative degradation of polyolefins as described in U.S. Pat. No. 4,100,132. U.S. Pat. No. 4,147,689 discloses use of bis(alkylhydroxyphenylacyl) 3,3' thiadicarboxylic acid dihydrazides as thermal antioxidants for polyolefins as they demonstrate combined properties of a primary antioxidant, a secondary antioxidant and a copper deactivator. U.S. Pat. No. 4,557,844 discloses aminated boron, phosphorus and nitrogen containing reaction products as antioxidants and antifriction agents that hinder the corrosion of copper. Mixed alkoxylated alcohol-hydroquinone or alkoxylated alcohol-resorcinol borates have also been reported in U.S. Pat. No. 4,985,157, to be multifunctional antioxidants for lubricants. EP0705874 discloses a process for stabilization of organic material by incorporating either of the proposed two structural varieties of multifunctional antioxidants. U.S. Pat. No. 6,444,733 provides structural possibilities of various organic phosphites and phosphonites for use as antioxidants during polyolefin stabilization. US Applications 2008293856A1 and 2005209379A1 and U.S. Pat. No. 4,739,090 disclose various phosphorus stabilizers amongst spiro diphenyl pentaerythritol diphosphites along with their preparation methods, for polyolefin stabilization.

In spite of considerable advances in the science of antioxidants, there still remain substantial shortcomings that need to be overcome. The still widely prevalent practice of concurrent use of primary and secondary antioxidants not only increases the cost of the process but also increases the risk to environment due to the use of a large number of additives. Further, a majority of the commonly prevalent antioxidants are low molecular weight species and are thus highly volatile. Thus, upon exposure to severe polymer processing conditions, the low molecular weight antioxidants undergo volatilization and get removed from the process, thereby exhibiting only a short-term effect. Even further, efficiency of many antioxidants is less which causes just partial stabilization of the polymers, eventually leading to undue coloration of polymer products. Also, multifunctional antioxidants have only recently become available and most of the reported varieties fall short of achieving the desired stabilizing effect.

The need for developing new high molecular weight, less volatile, multifunctional and more efficient antioxidants is thus evident. The present disclosure provides tetraoxa phosphaspiro compounds that strive to overcome the aforementioned shortcomings.

OBJECTS

Some of the objects of the present disclosure are discussed herein below:

It is an object of the present disclosure to provide tetraoxa diphosphaspiro compounds.

It is another object of the present disclosure to provide tetraoxa diphosphaspiro compounds which possess multifunctional attributes.

It is yet another object of the present disclosure to provide tetraoxa diphosphaspiro compounds which are capable of stabilizing polymers.

It is still another object of the present disclosure to provide a process for synthesizing tetraoxa diphosphaspiro compounds.

It is still another object of the present disclosure to provide a composition comprising pre-determined amount of tetraoxa diphosphaspiro compounds.

It is further object of the present disclosure to provide a polymeric blend comprising pre-determined amount of tetraoxa diphosphaspiro compounds.

It is still another object of the present disclosure to ameliorate one or more problems of the prior art or to at least provide a useful alternative.

Other objects and advantages of the present disclosure will be more apparent from the following description which is not intended to limit the scope of the present disclosure.

SUMMARY

In one aspect of the present disclosure there is provided a tetraoxa diphosphaspiro compound of formula I,

FORMULA I

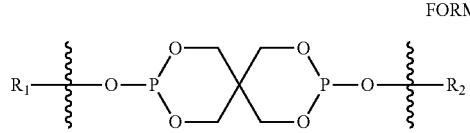

wherein;

$R_1$ and $R_2$ are represented by at least one fragment selected from the group consisting of formula Ia and Ib, Ia

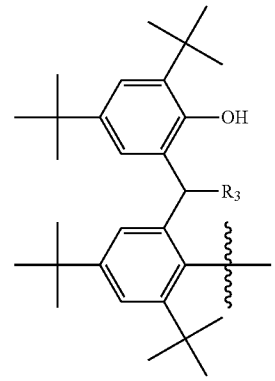

Ib

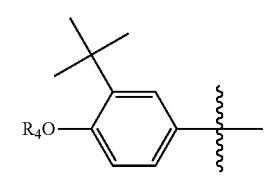

wherein;

$R_3$ is at least one selected from the group consisting of hydrogen, $C_1$-$C_{10}$ substituted or unsubstituted, linear or branched alkyl group and aryl group, preferably $C_1$ unsubstituted alkyl group;

$R_4$ is at least one selected from the group consisting of $C_1$-$C_{10}$ substituted or unsubstituted, linear or branched alkyl group and aryl group, preferably $C_1$ unsubstituted alkyl group; and

indicates the point of attachment.

In one of the preferred embodiments of the present disclosure a tetraoxa diphosphaspiro compound is of formula IV;

Formula IV

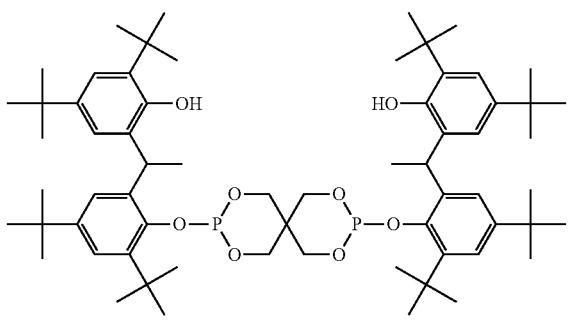

In another preferred embodiment of the present disclosure a tetraoxa diphosphaspiro compound is of formula V;

Formula V

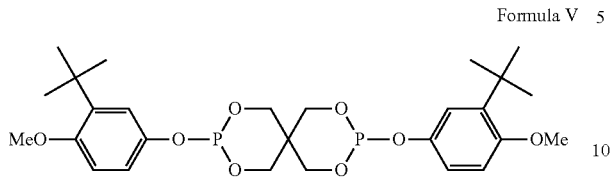

In still another preferred embodiment of the present disclosure a tetraoxa diphosphaspiro compound is of formula VI;

Formula VI

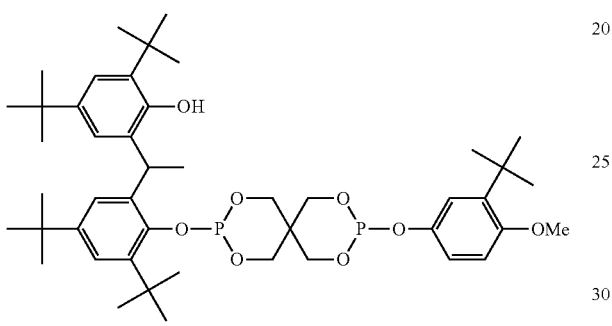

In accordance with another aspect of the present disclosure there is provided a process for synthesizing tetraoxa diphosphaspiro compound of formula I, said process comprising the following steps:

i. refluxing at a temperature ranging between 40° C. and 80° C., at least one phenolic compound, at least one phosphorus donor and at least one polyhydroxy compound, in the presence of at least one first amine and at least one aromatic solvent to obtain a first reaction mixture;

ii. removing excess of the phosphorous donor from the first reaction mixture by applying vacuum ranging between 200 and 700 mmHg, preferably between 250 and 600 mmHg to obtain a second reaction mixture;

iii. admixing at least one second amine and at least one phase transfer catalyst with the second reaction mixture to obtain a third reaction mixture;

iv. heating the third reaction mixture at a temperature ranging between 50° C. and 120° C., preferably between 77° C. and 83° C. to obtain a reaction mass;

v. allowing the reaction mass to stand at a temperature ranging between 20° C. and 35° C. for a time period ranging between 8.0 and 20.0 hours to obtain a slurry;

vi. filtering the slurry to obtain a filtrate; and vii. subjecting said filtrate to extraction using at least one extracting solvent to obtain the compound of formula (I).

Typically, the refluxing temperature ranges between 60° C. and 65° C.

Typically, the phenolic compound is at least one selected from the group consisting of mono-phenolic compounds and bis-phenolic compounds.

Typically, the mono-phenolic compound is represented by formula II,

FORMULA II

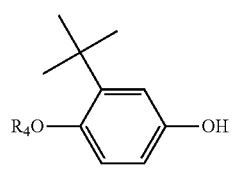

wherein, $R_4$ is at least one selected from the group consisting of $C_1$-$C_{10}$ substituted or unsubstituted, linear or branched alkyl group and aryl group, preferably $C_1$ unsubstituted alkyl group.

Typically, the bis-phenolic compound is represented by formula III,

FORMULA III

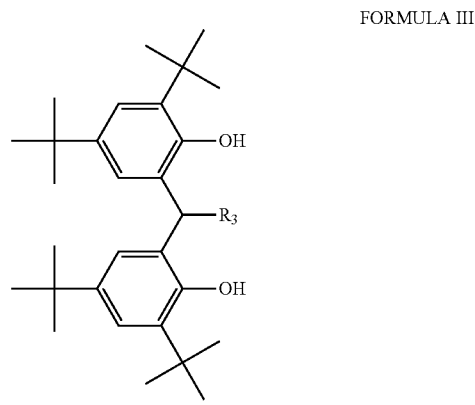

wherein;

$R_3$ is at least one selected from the group consisting of hydrogen, $C_1$-$C_{10}$ substituted or unsubstituted, linear or branched alkyl group and aryl group, preferably $C_1$ unsubstituted alkyl group.

Typically, the phosphorus donor is selected from the group consisting of phosphorus oxychloride, phosphorus trichloride, phosphorus pentachloride and phosphorous tribromide; preferably phosphorus trichloride.

Typically, the step of refluxing comprises adding the phosphorus donor in a drop-wise fashion to a mixture containing at least one phenolic compound, at least one polyhydroxy compound, at least one first amine and at least one aromatic solvent for a time period ranging between 0.5 and 3 hours, preferably between 0.5 and 1 hour at a temperature ranging between 15 and 35° C.

Typically, the polyhydroxy compound is pentaerythritol.

Typically, the first and second amine are same or different, said first and second amine being selected from the group of compounds comprising methylamine, ethylamine, trimethylamine, triethylamine, propylamine, isopropylamine, preferably triethylamine.

Typically, the aromatic solvent is selected from the group consisting of benzene, toluene, ethyl benzene, p-diethyl benzene, xylenes, chlorobenzene, dichlorobenzenes and trichlorbenzene; preferably, toluene.

Typically, the step of refluxing is carried out under inert atmosphere with constant stirring.

Typically, the step of refluxing is carried out under nitrogen atmosphere.

Typically, the step of refluxing is carried out for a time period ranging between 0.5 and 3 hours, preferably between 1 and 2 hours.

Typically, the step of applying vacuum is carried out for a time period ranging between 0.5 and 3 hours, preferably between 1 and 2 hours.

Typically, the phase transfer catalyst is selected from the group consisting of benzyltrimethylammonium chloride, hexadecyltributylphosphonium bromide, tetraethyl ammonium bromide, tetra-n-butyl ammonium bromide and methyltrioctylammonium chloride, preferably, tetraethyl ammonium bromide.

Typically, the step (iv) of heating is carried out for a time period ranging between 1.0 and 5.0 hours, preferably between 2.5 and 3.5 hours.

Typically, the step (v) is carried out at a temperature ranging between 20° C. and 30° C. for a time period ranging between 12 and 18 hours.

Typically, the extracting solvent is selected from the group consisting of petroleum ether, diethyl ether, dibutyl ether, tetrahydrofuran (THF), methanol, ethanol, butanol, acetone, methyl ethyl ketone and diethyl ketone.

In accordance with still another aspect of the present disclosure there is provided a composition comprising:
i. a pre-determined amount of tetraoxa diphosphaspiro compound of formula I;

FORMULA I

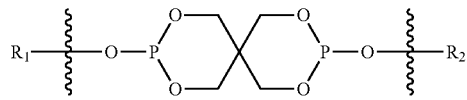

wherein;
$R_1$ and $R_2$ are represented by at least one fragment selected from the group consisting of formula Ia and Ib, Ia

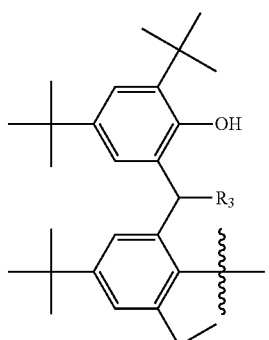

Ib

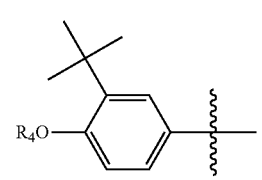

wherein;
$R_3$ is at least one selected from the group consisting of hydrogen, $C_1$-$C_{10}$ substituted or unsubstituted, linear or branched alkyl group and aryl group, preferably $C_1$ unsubstituted alkyl group;
$R_4$ is at least one selected from the group consisting of $C_1$-$C_{10}$ substituted or unsubstituted, linear or branched alkyl group and aryl group, preferably $C_1$ unsubstituted alkyl group; and

indicates the point of attachment, and
ii. optionally, at least one excipient.

In yet another aspect of the present disclosure there is provided a polymeric blend comprising:
i. at least one polymeric substrate,
ii. a pre-determined amount of tetraoxa diphosphaspiro compound of formula I;

FORMULA I

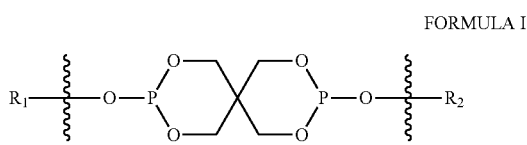

wherein;
$R_1$ and $R_2$ are represented by at least one fragment selected from the group consisting of formula Ia and Ib, Ia

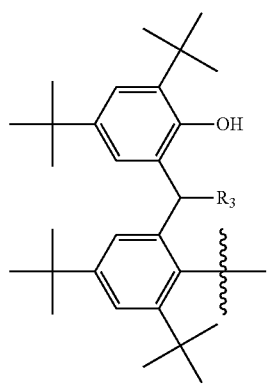

Ib

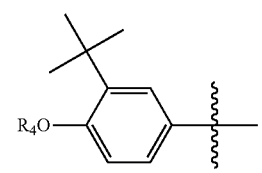

wherein;
$R_3$ is at least one selected from the group consisting of hydrogen, $C_1$-$C_{10}$ substituted or unsubstituted, linear or branched alkyl group and aryl group, preferably $C_1$ unsubstituted alkyl group;

$R_4$ is at least one selected from the group consisting of $C_1$-$C_{10}$ substituted or unsubstituted, linear or branched alkyl group and aryl group, preferably $C_1$ unsubstituted alkyl group; and

indicates the point of attachment, and
iii. optionally, at least one excipient.

Typically, the polymeric substrate is at least one selected from the group consisting of polyolefins, polyolefin co-polymers, polystyrenes, poly-(p-methylstyrene), polystyrene co-polymers, graft co-polymers of styrene, halogen containing polymers, polyacrylates, polymethacrylates, polyacrylamides, polyacrylonitriles, polyvinyl alcohols, polyvinyl acetates, polyvinyl stearates, polyvinyl benzoates, polyvinyl maleates, polyvinylbutyrals, polyallyl phthalates, polyallylmelamines, polyalkylene glycols, polyethylene oxides, polypropylene oxides, polyacetals, polyphenylene oxides, polyphenylene sulfides, polyurethanes, polyethers, polyesters, polyisocyanates, polyols, polyamides, co-polyamides, polyureas, polyimides, polyamide-imides, polycarbonates, polysulfones, polyethersulfones, polyetherketones, unsaturated polyester resins, acrylic resins, alkyd resins, polyisocyanates, polyepoxides, natural polymers, modified natural polymers, oils, animal fats, vegetable fats natural rubber, synthetic rubber, polysiloxanes polyketimines and oils, fats and waxes based on phthalates, adipates, phosphates and trimellitates, In further aspect of the present disclosure a compound of formula I is used as a stabilizer in a pre-determined amount for stabilizing polymers;

FORMULA I

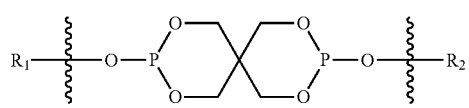

wherein;
$R_1$ and $R_2$ are represented by at least one fragment selected from the group consisting of formula Ia and Ib,

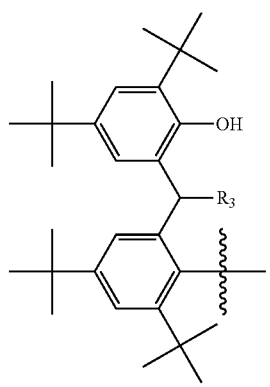

Ia

-continued

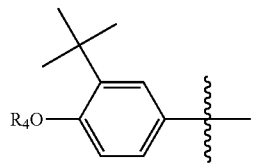

Ib wherein;
$R_3$ is at least one selected from the group consisting of hydrogen, $C_1$-$C_{10}$ substituted or unsubstituted, linear or branched alkyl group and aryl group, preferably $C_1$ unsubstituted alkyl group;
$R_4$ is at least one selected from the group consisting of $C_1$-$C_{10}$ substituted or unsubstituted, linear or branched alkyl group and aryl group, preferably $C_1$ unsubstituted alkyl group; and

indicates the point of attachment

DETAILED DESCRIPTION

The present disclosure relates to a secondary functional and multifunctional diphosphaspiro compounds. The diphosphaspiro compounds of instant disclosure are structurally distinguished from the diphosphaspiro compounds of the prior art, and provide efficient functional performance.

The tetraoxa diphosphaspiro compounds of the present disclosure are represented by Formula I.

FORMULA I

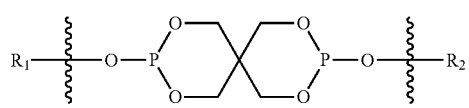

In the said formula, $R_1$ and $R_2$ are represented by at least one fragment selected from the group consisting of formula Ia and Ib,

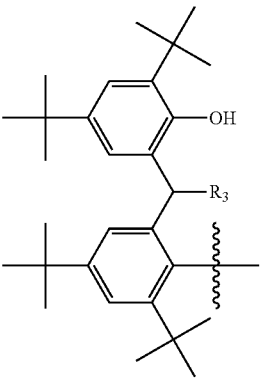

Ia

-continued

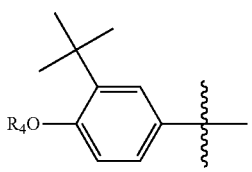

Ib

R₃ in fragment Ia may be selected from the group consisting of Hydrogen, $C_1$-$C_{10}$ substituted or unsubstituted, linear or branched alkyl group and aryl group and is preferably $C_1$ unsubstituted alkyl group. Similarly, in fragment Ib, $R_4$ may be selected from the group consisting of $C_1$-$C_{10}$ substituted or unsubstituted, linear or branched alkyl group and aryl group and is preferably C1 unsubstituted alkyl group. It is to be noted that the sign

indicates the point of attachment.

Methyl group is the most preferred $C_1$ unsubstituted alkyl group in the fragments Ia and Ib.

In one of the preferred embodiments of the present disclosure there is provided a tetraoxa diphosphaspiro compound represented by formula IV;

Formula IV

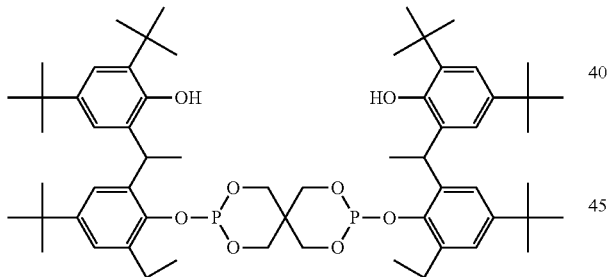

In another preferred embodiment of the present disclosure there is provided a tetraoxa diphosphaspiro compound represented by formula V.

Formula V

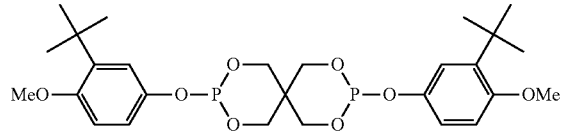

In yet another preferred embodiment of the present disclosure there is provided a tetraoxa diphosphaspiro compound represented by formula VI.

Formula VI

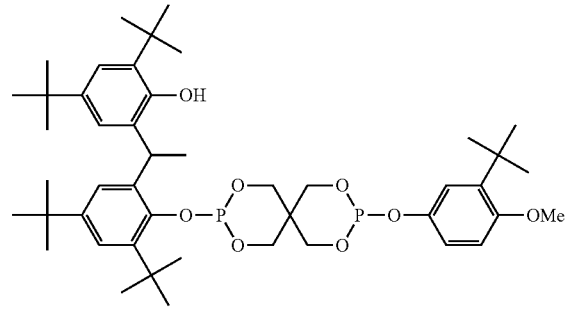

In another aspect of the present disclosure there is provided a process for synthesizing the hitherto mentioned tetraoxa diphosphaspiro compound represented by Formula I.

In the first step of the said process, at least one phenolic compound, at least one phosphorus donor and at least one polyhydroxy compound are refluxed in the presence of at least one first amine and at least one aromatic solvent to form a first reaction mixture. The temperature at which refluxing is carried out ranges between 40° C. and 80° C. and the preferable refluxing temperature ranges between ranges between 60° C. and 65° C. The refluxing is carried out under inert atmosphere of nitrogen with constant stirring for a time period ranging between 0.5 and 3 hours, preferably between 1 and 2 hours.

The phenolic compounds are selected from the group consisting of mono-phenolic compounds and bis-phenolic compounds. The mono-phenolic compound is represented by Formula II.

FORMULA II

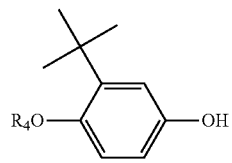

$R_4$ in Formula II may be selected from the group consisting of $C_1$-$C_{10}$ substituted or unsubstituted, linear or branched alkyl group and aryl group, and is preferably $C_1$ unsubstituted alkyl group. The bis-phenolic compound is represented by Formula III.

FORMULA III

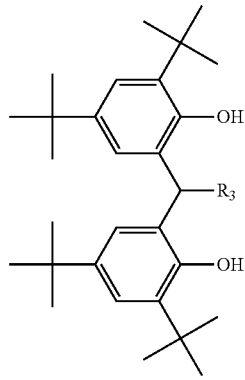

$R_3$ in Formula III may be selected from the group consisting of hydrogen, $C_1$-$C_{10}$ substituted or unsubstituted, linear or branched alkyl group and aryl group, and is preferably $C_1$ unsubstituted alkyl group.

The phosphorus donor employed is selected from the group consisting of phosphorus oxychloride, phosphorus trichloride, phosphorus pentachloride, phosphorous tribromide and is preferably phosphorus trichloride.

The method step of refluxing comprises the addition of said phosphorus donor in a drop-wise fashion into a mixture containing at least one phenolic compound, at least one polyhydroxy compound, at least one first amine and at least one aromatic solvent for a time period ranging between 0.5 and 3 hours, and the preferred time period ranges between 0.5 and 1 hour. The addition of the phosphorous donor is carried out at a temperature ranging between 15 and 35° C. The polyhydroxy compound particularly used for synthesizing compounds of formula I is pentaerythritol. The aromatic solvent is selected from the group consisting of benzene, toluene, ethyl benzene, p-diethyl benzene, xyleneschlorobenzene, dichlorobenzene, trichlorobenzene and is preferably, toluene. Refluxing is carried out for a time period ranging between 0.5 and 3 hours and occurs under inert atmosphere, preferably nitrogen atmosphere, with constant stirring. The preferred time period for refluxing ranges between 1 and 2 hours.

The afore-stated process step is vital as the bonding between phosphorus donor and phenolic precursor provides multifunctional attributes to the resulting compound of formula I whereas the bonding of polyhydroxy compound ensures high melting and consequently low volatility characteristics of the compound of formula I. These acquired characteristics make the compound of formula I long lasting and efficient in reducing the rate of degradation when used in polymers.

In the second step, vacuum ranging between 200 and 700 mmHg is applied to the first reaction mixture to remove excess of the phosphorus donor. Preferably, 250-600 mmHg range vacuum is applied for a time period ranging between 0.5 and 3 hours, to obtain a second reaction mixture. Preferably, 1-2 hours is the time period required for this step.

In the third step, the second reaction mixture is admixed with at least one second amine and at least one phase transfer catalyst to form a third reaction mixture. The third reaction mixture is heated at a temperature ranging between 50° C. and 120° C., where the preferable heating temperature ranges from 77° C. to 83° C. to obtain a reaction mass. Heating is carried out for a time period ranging between 1.0 and 5.0 hours, where 2.5-3.5 hours is the preferred time period. The first amine and second amine may be selected from the group of compounds comprising methylamine, ethylamine, trimethylamine, triethylamine, propylamine, isopropylamine. The first amine employed in the first process step and the second amine in the third step may be same or may be different. The first and second amine is preferably triethylamine. The phase transfer catalyst may be selected from the group consisting of benzyltrimethylammonium chloride, hexadecyltributylphosphonium bromide, tetraethyl ammonium bromide, tetra-n-butyl ammonium bromide or methyltrioctylammonium chloride and is preferably tetraethyl ammonium bromide.

In the next step, the obtained reaction mass is allowed to stand at a temperature ranging between 20° C. and 35° C., for a time period ranging between 8.0 and 20.0 hours to provide slurry. Preferably, the reaction mass is allowed to stand at a temperature ranging between 20° C. and 30° C., for a time period ranging between 12.0 and 18.0 hours to provide slurry.

Finally, the slurry after standing is subjected to filtration and the filtrate is further extracted to provide the compound represented by Formula I. The extracting solvent is selected from the group of solvents consisting of aliphatic hydrocarbons like petroleum ether, ethers like diethyl ether, dibutyl ether and tetrahydrofuran (THF), alcohols like methanol, ethanol and butanol and ketones like acetone, methyl ethyl ketone and diethyl ketone.

In another aspect of the present disclosure there is provided a composition comprising a pre-determined amount of tetraoxa diphosphaspiro compound of formula I and optionally, at least one excipient. The formula I and the substituents of formula I present in the composition are as described above.

In still another aspect of the present disclosure there a polymeric blend comprising at least one polymeric substrate, a pre-determined amount of tetraoxa diphosphaspiro compound of formula I and optionally, at least one excipient. The formula I and the substituents of formula I present in the polymeric blend are as described above.

The polymeric substrate in the polymeric blend is at least one selected from the group consisting of polyolefins, polyolefin co-polymers, polystyrenes, poly-(p-methylstyrene), polystyrene co-polymers, graft co-polymers of styrene, halogen containing polymers, polyacrylates, polymethacrylates, polyacrylamides, polyacrylonitriles, polyvinyl alcohols, polyvinyl acetates, polyvinyl stearates, polyvinyl benzoates, polyvinyl maleates, polyvinylbutyrals, polyallyl phthalates, polyallyl-melamines, polyalkylene glycols, polyethylene oxides, polypropylene oxides, polyacetals, polyphenylene oxides, polyphenylene sulfides, polyurethanes, polyethers, polyesters, polyisocyanates, polyols, polyamides, co-polyamides, polyureas, polyimides, polyamide-imides, polycarbonates, polysulfones, polyethersulfones, polyetherketones, unsaturated polyester resins, acrylic resins, alkyd resins, polyisocyanates, polyepoxides, natural polymers, modified natural polymers, oils, animal fats, vegetable fats natural rubber, synthetic rubber, polysiloxanes polyketimines and oils, fats and waxes based on phthalates, adipates, phosphates and trimellitates.

The excipient used in the composition and the polymeric blend of the present disclosure includes but is not limited to surfactants, pH modifiers, preservatives, adjuvants, antifreezes, oils, waxes, thickening agents (gelling agent), emollients, alkalizing agents, acidifying agents, perfumes, binding agents, defoamers, stabilizing agents, dispersing agents, wetting agents, colorants, vehicles and emulsifiers.

In yet another aspect of the present disclosure a compound of formula I is used as a stabilizer in a pre-determined amount for stabilizing polymers.

The disclosure will now be explained with the help of the following non-limiting examples.

The compounds of the present disclosure were synthesized and evaluated for anti-oxidation properties.

Example 1

Synthesis of 3,9-bis(2,2'-ethylidenebis(4,6-ditertiary-butyl-1-hydroxyphenoxy)2,4,8,10-tetreaoxa-3,9-diphosphaspiro(5,5)undecane[Multifunctional Antioxidant or MFAO] Formula IV In a round bottom flask containing a mixture of 9.1 g of 2,2'-ethylidene bis(4,6-di-t-butyl) phenol [procured from Aldrich, USA], 1.5 g of pentaerythritol, 0.07 g of triethylamine ($Et_3N$) and 10 g of toluene, 3.15 g of phosphorus trichloride ($PCl_3$) was added drop-wise over a period of 1 hour. After stirring the mixture at 65° C. for 1.5 hours under nitrogen atmosphere, it was subjected to 600 mmHg of vacuum for a period of 1.5 hours to remove excess PCl₃ and to obtain a reaction mixture. 2.44 g of Et₃N and 0.070 g of tetraethylammoniumbromide (Et₄NBr) were added to this reaction mixture and heated at 80° C. for 3 hours to provide a reaction mass. The reaction mass was then allowed to stand for 16 hours at 25° C., followed by filtration to remove the salt formed. 20 ml of methanol was then added to the filtrate and the mixture was further allowed to stand for 1 hour. The solid formed was filtered out and dried to obtain 2 g of 3,9-bis(2, 2'-ethylidenebis(4,6-ditertiarybutyl-1-hydroxyphenoxy)2,4, 8,10-tetreaoxa-3,9-diphosphaspiro(5,5)undecane i.e. the multifunctional antioxidant (MFAO). Melting point of the resultant multifunctional antioxidant was found to be 255° C. Molecular weight—1068 (m/e), Elemental Analysis: C=72.9% (73% theoretical), H=9% (9.18 Theoretical). Reaction mechanism for synthesis of Multifunctional Antioxidant (MFAO) Formula IV is represented herein below;

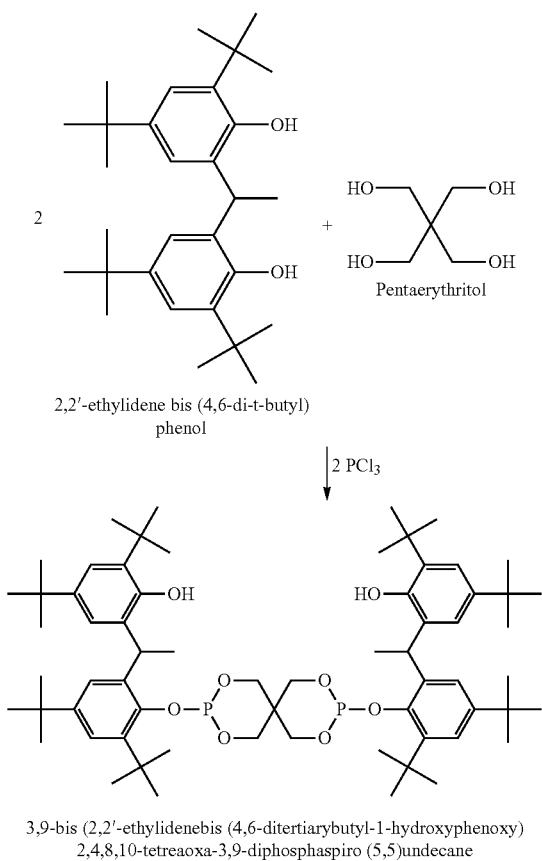

The reaction mixture was subjected to 250 mmHg of vacuum for a period of 1.5 hours to remove excess PCl₃. To this mixture 2.44 g of Et₃N and 0.07 g of Et₄NBr was added and heated at 80° C. for 3 hours. The mixture was allowed to stand for 16 hours at 25° C. and the salt formed was removed by filtration. 50 ml petroleum ether was added to the filtrate resulting in the precipitation of pink colored solid. The filtrate containing pink colored solid was cooled in a freezer and extracted using toluene. Petroleum ether was again added to the filtrate to separate an oily layer. The oily layer was later collected, concentrated, thawed, filtered and dried to obtain 2.5 g of 3,9-bis(4-methoxy-3-t-butylphenoxy)2,4,8,10-tetreaoxa-3,9-diphosphaspiro(5,5)undecane i.e. secondary antioxidant (SAO) as a white precipitate. The filtrate also yielded 0.83 g crude SAO. A total of 3.33 g of the SAO showed a melting point of 152-155° C. Molecular weight—552 (m/e), Elemental Analysis: C=58.65% (Theoretical—58.7%), H=6.8% (Theoretical—6.88%). Reaction mechanism for synthesis of Secondary Antioxidant (SAO) Formula V is represented herein below:

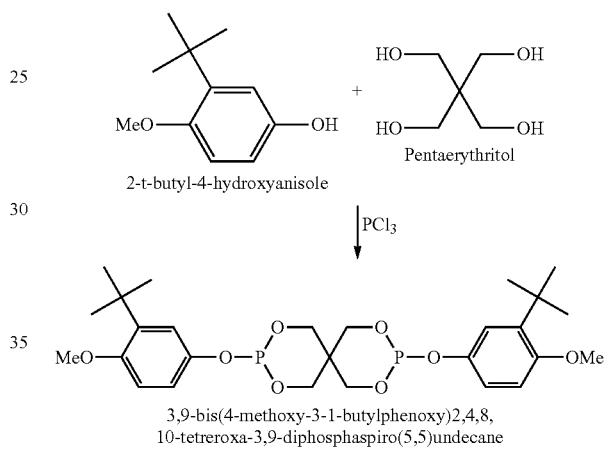

In order to gauge the efficacy of the multifunctional and secondary antioxidants, stabilization studies were conducted. Various resultant stabilized compositions were evaluated by comparing values of thermal stability, melt flow index, melt flow ratio, yellowness index and whiteness index with those of the reference polypropylene compositions.

Example 3

Preparation of Reference Polypropylene-Homopolymer Composition (REF-PPHP)

1000 ppm Vaseline oil was placed in a Brabender Plasticorder ribbon mixer and heated to 120° C. 350 ppm of Irganox 1076 (commercially available primary antioxidant), 150 ppm of PEPQ (commercially available secondary antioxidant), 100 ppm of Irgafos 168 (commercially available secondary antioxidant) and 500 ppm of Irganox 1010 (commercially available primary antioxidant) were added to the Vaseline oil and heated for 5 minutes. Polypropylene (PP), homopolymer (un-stabilized 1000 gm, Melt index 3 gm/10 min) was added and mixed for 5 minutes at the same temperature. 500 ppm calcium stearate was added, mixed for 15-20 minutes at 70 rotations per minute (rpm) to form a composition and kept in a sealed bag purged with nitrogen. The ribbon mixer of the Brabender Plasticorder was then replaced by a single screw Example 2

Synthesis of 3,9-bis(4-methoxy-3-t-butylphenoxy)2, 4,8,10-tetreaoxa-3,9-diphosphaspiro(5,5)undecane [Secondary Antioxidant or SAO] Formula V In a round bottom flask containing 3.9 g of 2-t-butyl-4-hydroxy anisole (TBHA) [procured from M/s Triveni Chemicals, Vapi, Gujarat, India], 1.5 g of pentaerythritol, 0.07 g of Et₃N and 15 ml of toluene, 3.25 g of PCl₃ was added over a time period of 30 minutes followed by stirring at 60° C. for 2 hours under nitrogen atmosphere to obtain a reaction mixture.

extruder and the composition kept in the sealed bag was extruded at a temperature profile of 180-210-235-230° C. with a screw rpm of 50. The extrudates were cooled, pelletized into 2-3 mm granules and dried at 80° C. for 2 hours.

Example 4

Preparation of PPHP-SAO (Formula V) Composition

The commercially available secondary antioxidant PEPQ (150 ppm) were substituted with 150 ppm of the secondary antioxidant (SAO) prepared in Example 2 and composition granules were prepared as per the procedure given in Example 3.

Example 5

Preparation of PPHP-MFAO (Formula IV) Composition

The commercially available secondary antioxidant PEPQ (150 ppm) and the commercially available primary antioxidant Irganox 1076 (350 ppm) were substituted with 150 ppm of the multifunctional antioxidant (MFAO), prepared in Example 1 and the composition granules were prepared as per the procedure given in Example 3.

Example 6

Preparation of Reference Polypropylene-Copolymer Composition (REF-PPCP)

Polypropylene copolymer (PPCP, un-stabilized, 1000 gm., MFI—3.5 g/10 min) was placed in a Branbery mixer and admixed with 300 ppm of Irgafos 168 (commercially available secondary antioxidant), 500 ppm of Irganox 1010 (commercially available primary antioxidant), 0.40 g (500 ppm) of calcium stearate and 300 ppm of Atmer—129, for 30 minutes. This mass was extruded in a single screw extruder at a temperature profile of 180-210-235-230° C. at 50 rpm. The extrudate was cooled and dried as in Example 3.

Example 7

Preparation of PPCP-MFAO (Formula IV) Composition

The commercially available primary and the secondary antioxidants Irganox 1010 (500 ppm) and Irgafos 168 (300 ppm) respectively, were replaced by 400 ppm of the multifunctional antioxidant (MFAO) prepared in Example 1 and granules were prepared as per the procedure given in Example 6.

Example 8

Preparation of PPCP-SAO (Formula V) Composition

The commercially available secondary antioxidant Irgafos 168 (300 ppm) was substituted with 160 ppm of the secondary antioxidant (SAO) prepared in Example 2 and granules were prepared as per the procedure given in Example 6.

Example 9

Evaluation of Antioxidant Stability

As mentioned previously, the antioxidant ability of the secondary and multifunctional antioxidants, on incorporation with PPHP and PPCP, was assessed by carrying out Multiple Extrusions Test where the polymers were extruded from one to five times in a Brabender Plasticorder extruder at a temperature profile of 180-210-235-230° C., at 50 rpm. The extruded granules were evaluated for:
  a) Melt Flow Index (MFI) and Melt Flow Ratio (MFR) by measuring values after each extrusion as per the ASTM method ASTM D-1238-86 at 230° C./2.16 kg load.
  b) Yellowness Index (YI), Whiteness Index (WI) by measuring the colour obtained during multiple extrusions, on Hunter Lab and D25M as per ASTM D-1925-77.

TABLE 1

Evaluation of Secondary (SAO) (Formula V) and Multifunctional (MFAO) (Formula IV) for Melt Flow Index in Polypropylene homopolymer

| Polymer/ Antioxidants | Amount of antioxidant/s i.e., stabilizing agent/s | Multiple Extrusions (1-5)/ MFI (g/10 min) $1^{st}$ $2^{nd}$ $3^{rd}$ $4^{th}$ $5^{th}$ | MFR = MFI of $5^{th}$ extrusion/MFI of $1^{st}$ extrusion $5^{th}/1^{st}$ |
|---|---|---|---|
| REF-PPHP | Irganox 1076 = 350 ppm<br>PEPQ = 150 ppm<br>Irgafos 168 = 100 ppm<br>Irganox 1010 = 500 ppm<br>Total = 1100 ppm | 3.1  3.1  3.2  3.2  6.2 | 2.0 |
| PPHP-SAO (Formula V) | Irganox 1076 = 350 ppm<br>PEPQ = 0 ppm<br>SAO = 150 ppm<br>Irgafos 168 = 100 ppm<br>Irganox 1010 = 500 ppm<br>Total = 1100 ppm | 3.1  3.5  3.8  4.1  4.5 | 1.45 |
| PPHP-MFAO (Formula IV) | Irganox 1076 = 0 ppm<br>PEPQ = 0 ppm<br>MFAO = 150 ppm<br>Irgafos 168 = 100 ppm<br>Irganox 1010 = 500 ppm<br>Total = 750 ppm | 3.1  3.6  3.9  4.8  5.8 | 1.87 |

From the above results, it was observed that the compounds of the present invention when used as an anti-oxidant in the polypropylene homopolymers (PPHP), the resultant blend has lower values of melt flow index and melt flow ratio of the 5$^{th}$ extrusion to the 1$^{st}$ extrusion as compared to that of the reference polypropylene homopolymer.

Further, the total amount of antioxidants i.e. stabilizing agents required to obtain lower values of melt flow index and melt flow ratio of the 5$^{th}$ extrusion to the 1st extrusion in the presence of MFAO (Formula IV) in the polypropylene homopolymer is 31% lesser than that of the total amount of antioxidants (stabilizing agents) required in the reference polypropylene homopolymer.

TABLE 2

Evaluation of Secondary (SAO) (Formula V) and Multifunctional (MFAO) (Formula IV) for Yellowness Index in Polypropylene homopolymer

| Polymer/ Antioxidants | Amount of antioxidant/s i.e., stabilizing agent/s | Multiple Extrusions (1-5)/ Yellowness Index (YI) | | | | |
|---|---|---|---|---|---|---|
| | | 1$^{st}$ | 2$^{nd}$ | 3$^{rd}$ | 4$^{th}$ | 5$^{th}$ |
| REF -PPHP | Irganox 1076 = 350 ppm<br>PEPQ = 150 ppm<br>Irgafos 168 = 100 ppm<br>Irganox 1010 = 500 ppm<br>Total = 1100 ppm | 6 | 14 | 15 | 18 | 28 |
| PPHP-SAO (Formula V) | Irganox 1076 = 350 ppm<br>PEPQ = 0 ppm<br>SAO = 150 ppm<br>Irgafos 168 = 100 ppm<br>Irganox 1010 = 500 ppm<br>Total = 1100 ppm | 6 | 13 | 16 | 20 | 23 |
| PPHP-MFAO (Formula IV) | Irganox 1076 = 0 ppm<br>PEPQ = 0 ppm<br>MFAO = 150 ppm<br>Irgafos 168 = 100 ppm<br>Irganox 1010 = 500 ppm<br>Total = 750 ppm | 6 | 13 | 19 | 23 | 27 |

From the above results, it was observed that the compounds of the present invention when used as an anti-oxidant in the polypropylene homopolymers (PPHP), the resultant blend has lower values of yellowness index as compared to that of the reference polypropylene homopolymer.

Further, the total amount of antioxidants i.e. stabilizing agents required to obtain lower values of yellowness index in the presence of MFAO (Formula IV) in the polypropylene homopolymer is 31% lesser than that of the total amount of antioxidants (stabilizing agent) required in the reference polypropylene homopolymer.

TABLE 3

Evaluation of Secondary (SAO) (Formula V) and Multifunctional (MFAO) Formula IV) for Whiteness Index in Polypropylene homopolymer

| Polymer/ Antioxidants | Amount of antioxidant/s i.e., stabilizing agent/s | Multiple Extrusions (1-5)/ Whiteness Index (WI) | | | | |
|---|---|---|---|---|---|---|
| | | 1$^{st}$ | 2$^{nd}$ | 3$^{rd}$ | 4$^{th}$ | 5$^{th}$ |
| REF -PPHP | Irganox 1076 = 350 ppm<br>PEPQ = 150 ppm<br>Irgafos 168 = 100 ppm<br>Irganox 1010 = 500 ppm<br>Total = 1100 ppm | 44 | 32 | 27 | 25 | 19 |
| PPHP-SAO (Formula V) | Irganox 1076 = 350 ppm<br>PEPQ = 0 ppm<br>SAO = 150 ppm<br>Irgafos 168 = 100 ppm<br>Irganox 1010 = 500 ppm<br>Total = 1100 ppm | 43 | 27 | 21 | 14 | 10 |
| PPHP-MFAO (Formula IV) | Irganox 1076 = 0 ppm<br>PEPQ = 0 ppm<br>MFAO = 150 ppm<br>Irgafos 168 = 100 ppm<br>Irganox 1010 = 500 ppm<br>Total = 750 ppm | 44 | 26 | 16 | 9 | 5 |

From the above results, it was observed that the compounds of the present invention when used as an anti-oxidant in the polypropylene homopolymers (PPHP), the resultant blend has lower values of whiteness index as compared to that of the reference polypropylene homopolymer.

Further, the total amount of antioxidants i.e. stabilizing agents required to obtain lower values of whiteness index in the presence of MFAO (Formula IV) in the polypropylene homopolymer is 31% lesser than that of the total amount of antioxidants (stabilizing agent) required in the reference polypropylene homopolymer.

TABLE 4

Evaluation of Secondary (SAO) (Formula V) and Multifunctional (MFAO) (Formula IV) on Melt Flow Index in Polypropylene Copolymer

| Polymer/ Antioxidants | Amount of antioxidant/s i.e., stabilizing agent/s | Multiple Extrusions/ MFI (g/10 min) | | | | | MFR = MFI of 5$^{th}$ extrusion/MFI of 1$^{st}$ extrusion |
|---|---|---|---|---|---|---|---|
| | | 1$^{st}$ | 2$^{nd}$ | 3$^{rd}$ | 4$^{th}$ | 5$^{th}$ | 5$^{th}$/1$^{st}$ |
| REF-PPCP | Irgafos 168 = 300 ppm<br>Irganox 1010 = 500 ppm<br>Total = 800 ppm | 3.5 | 4.4 | 4.8 | 5.1 | 5.9 | 1.69 |
| PPHP-SAO (Formula V) | Irgafos 168 = 0 ppm<br>SAO = 160 ppm<br>Irganox 1010 = 500 ppm<br>Total = 660 ppm | 3.1 | 3.1 | 3.3 | 3.6 | 4.3 | 1.38 |
| PPHP-MFAO (Formula IV) | Irgafos 168 = 0 ppm<br>Irganox 1010 = 0 ppm<br>MFAO = 400 ppm<br>Total = 400 ppm | 3.5 | 4.3 | 4.6 | 5.3 | 5.6 | 1.60 |

From the above results, it was observed that the compounds of the present invention when used as an anti-oxidant in the polypropylene co-polymers (PPCP), the resultant blend has lower values of melt flow index and melt flow ratio of the 5$^{th}$ extrusion to the 1$^{st}$ extrusion as compared to that of the reference polypropylene copolymer.

Further, the total amount of antioxidants i.e. stabilizing agents required to obtain lower values of melt flow index and melt flow ratio of the 5$^{th}$ extrusion to the 1$^{st}$ extrusion in the presence of SAO (Formula V) and MFAO (Formula IV) in the polypropylene copolymer is 17.5% and 50% respectively lesser than that of the total amount of antioxidants (stabilizing agents) required in the reference polypropylene copolymer.

TABLE 5

Evaluation of Secondary (SAO) (Formula V) and Multifunctional (MFAO) (Formula IV) for Yellowness Index in Polypropylene copolymer

| Polymer/ Antioxidants | Amount of antioxidant/s i.e., stabilizing agent/s | Multiple Extrusions (1-5)/ Yellowness Index (YI) | | | | |
|---|---|---|---|---|---|---|
| | | 1$^{st}$ | 2$^{nd}$ | 3$^{rd}$ | 4$^{th}$ | 5$^{th}$ |
| REF-PPCP | Irgafos 168 = 300 ppm Irganox 1010 = 500 ppm Total = 800 ppm | 4 | 11 | 13 | 14 | 15 |
| PPHP-SAO (Formula V) | Irgafos 168 = 0 ppm SAO = 160 ppm Irganox 1010 = 500 ppm Total = 660 ppm | 4 | 7 | 12 | 13 | 15 |
| PPHP-MFAO (Formula IV) | Irgafos 168 = 0 ppm Irganox 1010 = 0 ppm MFAO = 400 ppm Total = 400 ppm | 6 | 9 | 13 | 13 | 16 |

From the above results, it was observed that the compounds of the present invention when used as an anti-oxidant in the polypropylene co-polymers (PPCP), the resultant blend has lower values of yellowness index as compared to that of the reference polypropylene copolymer.

Further, the total amount of antioxidants i.e. stabilizing agents required to obtain lower values of yellowness index in the presence of SAO (Formula V) and MFAO (Formula IV) in the polypropylene copolymer is 17.5% and 50% respectively, lesser than that of the total amount of antioxidants (stabilizing agents) required in the reference polypropylene copolymer.

TABLE 6

Evaluation of Secondary (SAO) (Formula V) and Multifunctional (MFAO) (Formula IV) for Whiteness Index in Polypropylene copolymer

| Polymer/ Antioxidants | Amount of antioxidant/s i.e., stabilizing agent/s | Multiple Extrusions (1-5)/ Whiteness Index (WI) | | | | |
|---|---|---|---|---|---|---|
| | | 1$^{st}$ | 2$^{nd}$ | 3$^{rd}$ | 4$^{th}$ | 5$^{th}$ |
| REF-PPCP | Irgafos 168 = 300 ppm Irganox 1010 = 500 ppm Total = 800 ppm | 64 | 44 | 39 | 36 | 33 |
| PPHP-SAO (Formula V) | Irgafos 168 = 0 ppm SAO = 160 ppm Irganox 1010 = 500 ppm Total = 660 ppm | 63 | 54 | 38 | 37 | 32 |
| PPHP-MFAO (Formula IV) | Irgafos 168 = 0 ppm Irganox 1010 = 0 ppm MFAO = 400 ppm Total = 400 ppm | 57 | 47 | 34 | 34 | 25 |

From the above results, it was observed that the compounds of the present invention when used as an anti-oxidant in the polypropylene co-polymers (PPCP), the resultant blend has lower values of whiteness index as compared to that of the reference polypropylene copolymer.

Further, the total amount of antioxidants i.e. stabilizing agents required to obtain lower values of whiteness index in the presence of SAO (Formula V) and MFAO (Formula IV) in the polypropylene copolymer is 17.5% and 50% respectively lesser than that of the total amount of antioxidants (stabilizing agents) required in the reference polypropylene copolymer.

From the results obtained above, it can be concluded that lower MFI, MFR, yellowness index and whiteness index values for polypropylene homopolymers and polypropylene copolymers comprising the compounds of the present invention is an indication of higher stability of antioxidant compared to the commercial antioxidants.

TABLE 7

Thermo-gravimetric Analysis data of (SAO) (Formula V) and Multifunctional (MFAO) (Formula IV) in Polypropylene Homopolymer and Copolymer

| Sr. No. | PP with MFAO | Decomposition Temperatures (° C.) | | |
|---|---|---|---|---|
| | | IDT | T$_{50}$ | T$_{100}$ |
| | Polypropylene Homopolymer | | | |
| 1 | REF-PPHP | 256 | 366 | 400 |
| 2 | PPHP-SAO (Formula V) | 266 | 371 | 400 |
| 3 | PPHP-MFAO (Formula IV) | 267 | 380 | 410 |
| | Polypropylene Copolymer | | | |
| 1 | REF-PPCP | 280 | 417 | 452 |
| 2 | PPHP-SAO (Formula V) | 309 | 417 | 453 |
| 3 | PPHP-MFAO (Formula IV) | 305 | 422 | 459 |

From the above results, the initial decomposition (IDT), 50 wt. % decomposition (T$_{50}$) and 100 wt. % decomposition temperatures (T$_{100}$) are higher in compositions prepared by using SAO (Formula V)/MFAO (Formula IV) compared to corresponding compositions prepared by using standard antioxidants. This clearly indicates that the compounds of the present invention provide higher thermal stability to the polymer.

TECHNICAL ADVANTAGES

The present disclosure, related to antioxidants for stabilizing polymers, has the following technical advantages:
(1) provides antioxidants having good miscibility in the polymers, and
(2) provides antioxidants that confer adequate stability to polymers, and
(3) provides antioxidants that preclude the need of including multiple additives for polymer stabilization; thereby reducing the total expenditure, and
(4) abridges the polymer composition and simplifies the storage and handling of various additives.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results.

The numerical values given for various physical parameters, dimensions and quantities are only approximate values and it is envisaged that the values higher than the numerical value assigned to the physical parameters, dimensions and quantities fall within the scope of the invention and the claims unless there is a statement in the specification to the contrary.

While certain embodiments of the inventions have been described, these embodiments have been presented by way of example only, and are not intended to limit the scope of the inventions. Variations or modifications in the process or compound or formulation or combination of this invention, within the scope of the invention, may occur to those skilled in the art upon reviewing the disclosure herein. Such variations or modifications are well within the spirit of this invention. The accompanying claims and their equivalents are intended to cover such forms or modifications as would fall within the scope and spirit of the invention.

The invention claimed is:

1. A tetraoxa diphosphaspiro compound of formula I,

FORMULA I

wherein;

$R_1$ and $R_2$ are represented by at least one fragment selected from the group consisting of formula Ia and Ib,

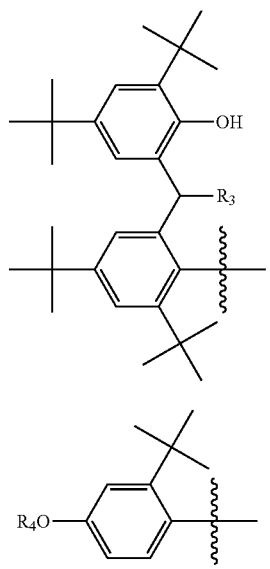

wherein;

$R_3$ is at least one selected from the group consisting of hydrogen, $C_1$-$C_{10}$ substituted or unsubstituted, linear or branched alkyl group and aryl group;

$R_4$ is at least one selected from the group consisting of $C_1$-$C_{10}$ substituted or unsubstituted, linear or branched alkyl group and aryl group; and

indicates the point of attachment.

2. The compound of claim 1, wherein said compound is of formula IV;

Formula IV

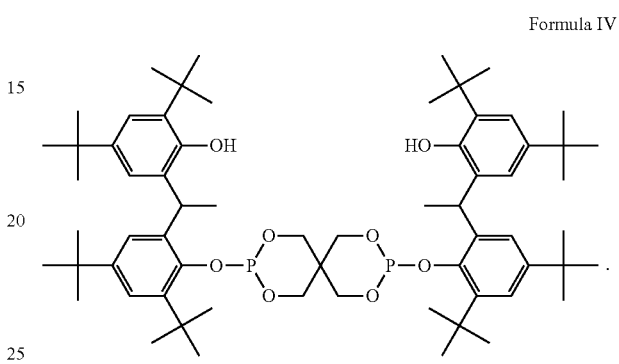

3. The compound of claim 1, wherein said compound is of formula V;

Formula V

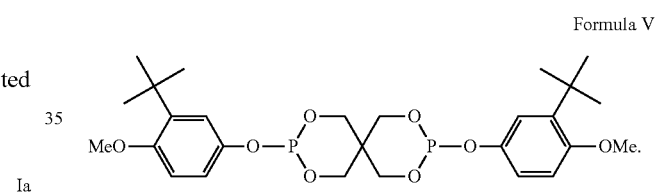

4. The compound of claim 1, wherein said compound is of formula VI;

Formula VI

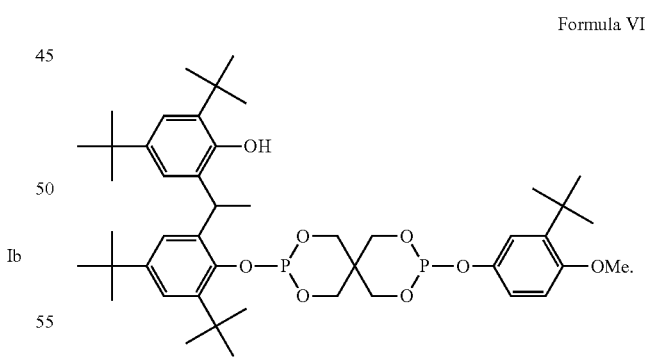

5. A process for synthesizing tetraoxa diphosphaspiro compound of formula I of claim 1, said process comprising the following steps:

i. refluxing at a temperature ranging between 40° C. and 80° C., at least one phenolic compound, at least one phosphorus donor and at least one polyhydroxy compound, in the presence of at least one first amine and at least one aromatic solvent to obtain a first reaction mixture;

ii. removing excess of the at least one phosphorous donor from the first reaction mixture by applying vacuum ranging between 200 and 700 mmHg to obtain a second reaction mixture;

iii. admixing at least one second amine and at least one phase transfer catalyst with the second reaction mixture to obtain a third reaction mixture;

iv. heating the third reaction mixture at a temperature ranging between 50° C. and 120° C. to obtain a reaction mass;

v. allowing the reaction mass to stand at a temperature ranging between 20° C. and 35° C. for a time period ranging between 8.0 and 20.0 hours to obtain a slurry;

vi. filtering the slurry to obtain a filtrate; and vii. subjecting said filtrate to extraction using at least one extracting solvent to obtain the compound of formula (I).

6. The process of claim 5, wherein the refluxing temperature ranges between 60° C. and 65° C.

7. The process of claim 5, wherein the at least one phenolic compound is selected from the group consisting of monophenolic compounds represented by formula (II);

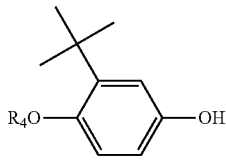

FORMULA II wherein;

$R_4$ is at least one selected from the group consisting of $C_1$-$C_{10}$ substituted or unsubstituted, linear or branched alkyl group and aryl group;

and bis-phenolic compounds represented by formula (III);

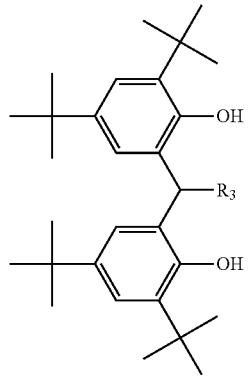

FORMULA III wherein;

$R_3$ is at least one selected from the group consisting of hydrogen, $C_1$-$C_{10}$ substituted or unsubstituted, linear or branched alkyl group and aryl group.

8. The process of claim 5, wherein the at least one phosphorus donor is selected from the group consisting of phosphorus oxychloride, phosphorus trichloride, phosphorus pentachloride and phosphorous tribromide.

9. The process of claim 5, wherein the step of refluxing comprises adding the at least one phosphorus donor in a drop-wise fashion to a mixture containing at least one phenolic compound, at least one polyhydroxy compound, at least one first amine and at least one aromatic solvent for a time period ranging between 0.5 and 3 hours and at a temperature ranging between 15 ° C.and 35° C.

10. The process of claim 5, wherein the at least one polyhydroxy compound is pentaerythritol.

11. The process of claim 5, wherein the at least one first and at least one second amine are same or different, said at least one first and at least one second amine being selected from the group of compounds comprising methylamine, ethylamine, trimethylamine, triethylamine, propylamine and isopropylamine.

12. The process of claim 5, wherein the at least one aromatic solvent is selected from the group consisting of benzene, toluene, ethyl benzene, p-diethyl benzene, xylenes, chlorobenzene, dichlorobenzenes and trichlorbenzene.

13. The process of claim 5, wherein the step of refluxing is carried out under inert atmosphere with constant stirring.

14. The process of claim 5, wherein the step of applying vacuum is carried out for a time period ranging between 0.5 and 3 hours.

15. The process of claim 5, wherein the at least one phase transfer catalyst is selected from the group consisting of benzyltrimethylammonium chloride, hexadecyltributylphosphonium bromide, tetraethyl ammonium bromide, tetra-n-butyl ammonium bromide and methyltrioctylammonium chloride.

16. The process of claim 5, wherein the step (iv) of heating is carried out for a time period ranging between 1.0 and 5.0 hours.

17. The process of claim 5, wherein the step (v) is carried out at a temperature ranging between 20° C. and 30° C. for a time period ranging between 12 and 18 hours.

18. The process of claim 5, wherein the at least one extracting solvent is selected from the group consisting of petroleum ether, diethyl ether, dibutyl ether, tetrahydrofuran (THF), methanol, ethanol, butanol, acetone, methyl ethyl ketone and diethyl ketone.

19. A composition comprising:

i. a pre-determined amount of tetraoxa diphosphaspiro compound Of formula I;

FORMULA I wherein;

$R_1$ and $R_2$ are represented by at least one fragment selected from the group consisting of formula Ia and Ib;

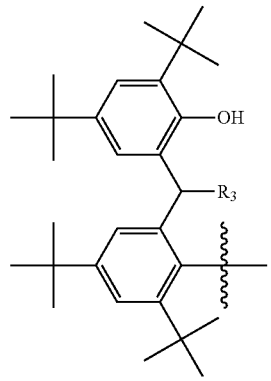

Ia

-continued

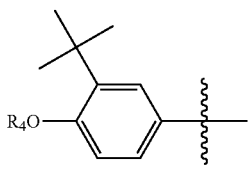

Ib wherein;
R₃ is at least one selected from the group consisting of hydrogen, $C_1$-$C_{10}$ substituted or unsubstituted, linear or branched alkyl group and aryl group;
R₄ is at least one selected from the group consisting of $C_1$-$C_{10}$ substituted or unsubstituted, linear or branched alkyl group and aryl group; and

indicates the point of attachment; and
ii. optionally, at least one excipient.

20. The composition of claim 19 being a polymeric blend and includes:
i. at least one polymeric substrate; and
ii. a pre-determined amount of tetraoxa diphosphaspiro compound of formula I;

FORMULA I

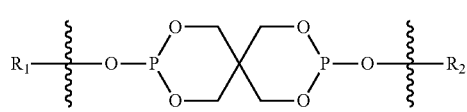

wherein;
R₁ and R₂ are represented by at least one fragment selected from the group consisting of formula Ia and Ib;

Ia

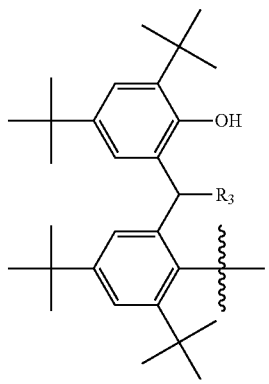

-continued

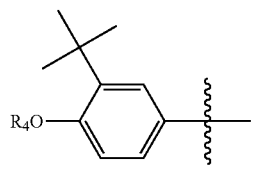

Ib wherein;
R₃ is at least one selected from the group consisting of hydrogen, $C_1$-$C_{10}$ substituted or unsubstituted, linear or branched alkyl group and aryl group;
R₄ is at least one selected from the group consisting of $C_1$-$C_{10}$ substituted or unsubstituted, linear or branched alkyl group and aryl group; and

indicates the point of attachment.

21. The composition of claim 20, wherein said at least one polymeric substrate is at least one selected from the group consisting of polyolefins, polyolefin co-polymers, polystyrenes, poly-(p-methylstyrene), polystyrene co-polymers, graft co-polymers of styrene, halogen containing polymers, polyacrylates, polymethacrylates, polyacrylamides, polyacrylonitriles, polyvinyl alcohols, polyvinyl acetates, polyvinyl stearates, polyvinyl benzoates, polyvinyl maleates, polyvinylbutyrals, polyallyl phthalates, polyallyl-melamines, polyalkylene glycols, polyethylene oxides, polypropylene oxides, polyacetals, polyphenylene oxides, polyphenylene sulfides, polyurethanes, polyethers, polyesters, polyisocyanates, polyols, polyamides, co-polyamides, polyureas, polyimides, polyamide-imides, polycarbonates, polysulfones, polyethersulfones, polyetherketones, unsaturated polyester resins, acrylic resins, alkyd resins, polyisocyanates, polyepoxides, natural polymers, modified natural polymers, oils, animal fats, vegetable fats natural rubber, synthetic rubber, polysiloxanes polyketimines and oils, fats and waxes based on phthalates, adipates, phosphates and trimellitates.

22. A stabilizer for stabilizing polymers, the stabilizer comprising the compound of claim 1.

* * * * *